(12) United States Patent
Kozlowski

(10) Patent No.: US 6,193,939 B1
(45) Date of Patent: Feb. 27, 2001

(54) APPARATUS FOR ULTRAVIOLET LIGHT TREATMENT OF FLUIDS

(76) Inventor: Henry Kozlowski, 39 Coach Lite Way, Willowdale, Ontario (CA), M2R 3J8

( * ) Notice: Subject to any disclaimer, the term of this patent is extended or adjusted under 35 U.S.C. 154(b) by 0 days.

(21) Appl. No.: 09/326,577

(22) Filed: Jun. 7, 1999

Related U.S. Application Data

(60) Provisional application No. 60/107,915, filed on Nov. 10, 1998.

(51) Int. Cl.[7] ............................... B01J 19/08; B01J 19/12
(52) U.S. Cl. .................. 422/186.3; 422/186; 422/186.07
(58) Field of Search .............................. 422/186, 186.3, 422/186.07

(56) References Cited

U.S. PATENT DOCUMENTS

| | | |
|---|---|---|
| 4,482,809 | 11/1984 | Maarschalkerweerd . |
| 4,872,980 | 10/1989 | Maarschalkerweerd . |
| 5,006,244 | 4/1991 | Maarschalkerweerd . |
| 5,019,256 | 5/1991 | Ifill et al. . |
| 5,070,277 | * 12/1991 | Lapatovich ............. 315/245 |
| 5,412,549 | 5/1995 | Blakely . |
| 5,418,370 | 5/1995 | Maarschalkerweerd . |
| 5,471,063 | 11/1995 | Hayes et al. . |
| 5,504,335 | 4/1996 | Maarschalkerweerd . |
| 5,539,209 | 7/1996 | Maarschalkerweerd . |
| 5,539,210 | 7/1996 | Maarschalkerweerd . |
| 5,590,390 | 12/1996 | Maarschalkerweerd . |
| 5,660,719 | 8/1997 | Kurtz et al. . |
| 5,853,676 | * 12/1998 | Morgan, Jr. ............ 422/186.3 |

\* cited by examiner

*Primary Examiner*—Kathryn Gorgos
*Assistant Examiner*—Wesley A. Nicolas
(74) *Attorney, Agent, or Firm*—Ridout & Maybee

(57) ABSTRACT

A process is described, for treating liquids with radiation. One process involves passing the liquid over an ultraviolet lamp and ballast assembly which is submerged in the liquid. Apparatus for the process has an elongate frame member which is immersed in the liquid. Attached to the frame member and immersed in the liquid is a plurality of ultraviolet lamps and associated ballasts.

17 Claims, 6 Drawing Sheets

APPARATUS FOR ULTRAVIOLET LIGHT TREATMENT OF FLUIDS

The present application claims the benefit of U.S. provisional application serial No. 60/107,915 filed Nov. 10, 1998.

FIELD OF THE INVENTION

The present invention relates to an apparatus for ultraviolet treatment of fluids such as water. More particularly, the present invention relates to an apparatus that employs a particular arrangement of ballasts and ultraviolet lamps.

BACKGROUND TO THE INVENTION

It is known to treat water with ultraviolet light in order to destroy undesirable bacteria and other microorganisms. For example, U.S. Pat. No. 5,660,719 which issued Aug. 26, 1997 to Kurtz et al. discloses an ultraviolet lamp rack assembly comprising an array of vertically disposed ultraviolet lamps for the treatment of fluids. The assembly has a separate enclosure for the housing at least one ballast and electronic components to power the lamps. Kurtz et al. indicate that substantial amounts of heat are generated during functioning of the ballast and that cooling is required. Cooling is provided by blowing air through the enclosure, or by means of air conditioning or the use of a heat exchanger.

Another arrangement is disclosed in U.S. Pat. No. 5,019,256 which issued May 28, 1991 to Ifill et al. This patent discloses an ultraviolet lamp rack assembly comprising a vertical array of horizontally disposed ultraviolet lamps for the treatment of waste water. A power control panel is provided at a location remote from the rack assembly for the inclusion of ballasts and various electronic components. Alternatively, the ballasts for the lamps may be located in a submerged vertical conduit which forms a part of the rack. One of the problems associated with such an arrangement is that the ballasts are difficult to remove from the rack, and if one ballast needs to be replaced then all of the ballasts must be removed. This is inefficient, as the ultraviolet treatment unit is out of service for a long period of time. Variations of the device of U.S. Pat. No. 5,019,256 to Ifill et al. are disclosed in U.S. Pat. Nos. 4,482,809, 4,872,980 and 5,006,244 to J. M. Maarschalkerweerd which issued Nov. 13, 1984, Oct. 10, 1989 and Apr. 9, 1991 respectively. The ballasts and power supply to the lamps are separate from the lamps and lamp racks.

Most commercial treatment systems for water, in which the water is treated with ultraviolet radiation, use ultraviolet lamps which have electrodes therein and are associated with ballasts. The present invention is also suitable for lamps which are electrodeless and are associated with high frequency excitation couplers. A description of a typical electrodeless lamp and coupler may be found in U.S. Pat. No. 5,070,277 to W. P. Lapatovich which issued Dec. 3, 1991.

The present invention attempts to overcome the deficiencies of the previous systems and provide a system which is easily maintained.

The term "wire", as used herein in relation to the present invention, includes a plurality of wires, e.g. as in a cable.

The terms "comprising/comprises" when used in this specification are taken to specify the presence of the stated features, integers, steps or components but do not preclude the presence or addition of one or more other features, integers, steps, components or groups thereof.

SUMMARY OF THE INVENTION

Accordingly, one aspect of the present invention provides a radiation source assembly for use with a fluid, comprising:

- at least one radiation source adapted to be immersed in said fluid when the assembly is in use, the source producing radiation by excitation of a gas;
- at least one excitation controlling means for controlling excitation of gas within the radiation source, said excitation controlling means being adapted to be immersed in said fluid when the assembly is in use;
- a first elongate frame member having a portion adapted to be immersed in the fluid when the assembly is in use, the frame member being connected to at least one of a) the radiation source and b) the excitation controlling means; and
- electrical conducting means for providing electrical energy to the excitation controlling means.

In one embodiment, the radiation source is a lamp for emitting ultraviolet radiation.

In another embodiment, the lamp has electrodes and the excitation controlling means is a ballast electrically connected to the lamp.

In a further embodiment, the lamp is an electrodeless lamp and the excitation controlling means is a high frequency coupler.

In another aspect of the present invention provides a radiation source assembly for use with a material selected from the group consisting of a liquid and a flowing fluid, comprising:

a) when the material is a liquid,
- at least one radiation source adapted to be immersed in said liquid when the assembly is in use;
- at least one excitation controlling means for controlling excitation of gas within the radiation source, said excitation controlling means being adapted to be immersed in said liquid when the assembly is in use;
- and electrical conducting means for providing electrical energy to the excitation controlling means; or b) when the material is a flowing fluid,
- at least one radiation source adapted to be immersed in said flowing fluid when the assembly is in use;
- at least one excitation controlling means for controlling excitation of gas within the radiation source, said excitation controlling means being adapted to be immersed in said flowing fluid when the assembly is in use;
- and electrical conducting means for providing electrical energy to the excitation controlling means.

In yet another embodiment, the radiation source assembly has a first elongate frame member having a portion adapted to be immersed in the liquid or flowing fluid when the assembly is in use, and the frame member is connected to at least one of the radiation source, a radiation-transparent sleeve for the radiation source and the excitation controlling means.

In a further embodiment, the radiation source is adjacent to the excitation controlling means.

In one embodiment, the radiation source is a lamp for emitting ultraviolet radiation.

In another embodiment, the lamp has electrodes and the excitation controlling means is a ballast electrically connected to the lamp.

In a further embodiment, the lamp is an electrodeless lamp and the excitation controlling means is a high frequency coupler.

In another embodiment, the ballast is supported by the first elongate frame member.

In a further embodiment, the ballast is elongate and has first and second opposed ends, the first end of which is mounted on said portion, the lamp is elongate and has first and second opposed ends, the first end of which is connected to the second end of the ballast.

In another embodiment, the lamp is elongate and has first and second ends, the first end of which is connected to the ballast and the second end of the lamp is supported by the first elongate frame member.

In a further embodiment, the assembly has a plurality of excitation controlling means, each with a radiation source associated therewith.

In yet another embodiment, the assembly has a plurality of radiation sources connected to each excitation controlling means.

In another embodiment, the electrical conducting means includes, for each excitation controlling means, an electrical wire which extends from the excitation controlling means to a location which is not immersed in the liquid or flowing fluid.

In a further embodiment, all of the electrical wires have a coating which is in contact with the liquid or flowing fluid.

In another embodiment, the assembly has a second elongate frame member, and when each ballast is supported by the first elongate frame member, the second end of each associated lamp is supported by said second elongate frame member.

In another embodiment, the ballast and lamp are encased in a transparent sleeve which is fluid-tight.

In a further embodiment, the transparent sleeve is mounted at a first end with a fluid-tight connection to the portion of the first elongate frame member.

In another embodiment, the transparent sleeve is mounted at the first end with a fluid-tight connection to the portion of the first elongate frame member, and mounted at a second end to the second elongate frame member.

In yet another embodiment, the first elongate frame member is tubular with an outer wall and, for each excitation controlling means, a support with an externally threaded tubular stub surrounding an access aperture through the outer wall, the excitation controlling means has an external retaining ring fixed adjacent the first end thereof, the assembly further comprising an internally threaded coupling for engaging the stub and the retaining ring, so as to move the stub and the ring toward each other, and a resilient sealing member between the stub and the coupling such that the retaining ring is pressed against the exterior of the excitation controlling means when the coupling is tightened.

In a further embodiment, the assembly has a sleeve surrounding each radiation source, said sleeve having one open end and one closed end and being made of a material transparent to radiation emitted by the radiation source, and a further coupling which sealingly supports the open end of said sleeve from the second end of the excitation controlling means.

In a further embodiment, the excitation controlling means is a ballast and the radiation source is a lamp with electrodes.

Another aspect of the invention provides an assembly for use in a photochemical treatment of a fluid, comprising:
   at least one radiation source for producing radiation by excitation of a gas;
   at least one excitation controlling means adapted to be immersed in said fluid when the assembly is in use, for controlling excitation of the gas within the radiation source;
   a submersible frame member having a portion adapted to be immersed in the fluid when the assembly is in use and having a plurality of supports, each support providing support for at least one of a) a radiation source,
   b) a radiation-transparent sleeve for the radiation source and b) an excitation controlling means; and
   electrical conducting means for providing electrical energy to the excitation controlling means.

In one embodiment for treatment of a liquid, the assembly is selected from the group consisting of
A) an assembly in which the excitation controlling means is a ballast, said ballast having a second end opposed to a first end, and said ballast having an outer sleeve which encloses components of the ballast, the sleeve being sealed to prevent ingress of liquid into the ballast, said ballast and support having connection means for mechanically connecting the first end of the ballast to the support;
   the radiation source is an elongate ultraviolet lamp having first and second opposed ends, said lamp and ballast having connection means for mechanically and electrically connecting the first end of the lamp to the second end of the ballast; and
   and the assembly has means for sealing the lamp against direct contact with the liquid;
B) an assembly in which the radiation source is an elongate ultraviolet lamp having connection means for mechanically connecting the lamp to the support;
   the excitation controlling means is a ballast, said lamp and ballast having means for electrically connecting them together; and
   the assembly has sealing means for sealing the lamp and ballast against direct contact with the liquid;
C) an assembly in which the radiation source is an elongate ultraviolet lamp;
   the excitation controlling means is a ballast, said lamp and ballast having means for electrically connecting them together;
   and the assembly has a sleeve covering and sealing the lamp and ballast against direct contact with the liquid, and the assembly has connection means for mechanically connecting the sleeve means to the support; and
D) an assembly in which the excitation controlling means is a ballast, having an outer sleeve which encloses components of the ballast, the sleeve being sealed to prevent ingress of liquid into the ballast, said ballast having connection means for mechanically connecting the ballast to the support;
   the radiation source is an elongate ultraviolet lamp having connection means for mechanically connecting the lamp to the support separately from the ballast, and means for sealing the lamp against direct contact with the liquid, said lamp and ballast having means for electrically connecting them together.

In another embodiment, the means for sealing the lamp in embodiments A), B) or D) is a sleeve which is transparent to ultraviolet radiation.

In a further embodiment, submersible frame member is tubular, and the support surrounds an aperture in a side wall of the frame member, and the assembly further includes 1) a first electrical connection between the ballast and electrically conductive means within the tubular frame member, said first electrical connection having the form of pins entering suitable sockets, and 2) a second electrical connection between the ballast and the ultraviolet lamp, said second electrical connection also having the form of pins entering suitable sockets.

In yet another embodiment, the assembly includes electrical power transmission means for transmitting electrical power from a power source to each ballast, said power transmission means being outside the submersible frame member.

Preferably, all connections are substantially water tight.

The present invention also provides an ultraviolet lamp assembly for submersion in a liquid, comprising a rack with a submersible conduit, and at least one submersible ultraviolet lamp with associated submersible ballast wherein the ultraviolet lamp is removably coupled, physically and electrically, to an associated ballast and the ballast is removably coupled, physically, to the conduit such that when submerged, liquid cannot enter the conduit through the lamp and ballast couplings.

In one embodiment, the conduit contains electrical power transmission means and the ballast is removably coupled, electrically, to the power transmission means.

In a further embodiment the power transmission means is selected from the group consisting of wire and electrically conductive strips.

In another embodiment, the ultraviolet lamp is encased in a sleeve which is transparent to ultraviolet light.

In a further embodiment, the conduit has a tubular stub attached thereto such that there is electrical communication between the ballast and the power transmission means.

In another embodiment, there is a screw coupling with a liquid tight seal between the lamp, sleeve and ballast.

In yet another embodiment, there is a screw coupling and a liquid tight seal between the ballast and the conduit.

In another embodiment, the liquid is water.

The invention also provides a process for treating liquids with ultraviolet light comprising passing the liquid over an ultraviolet lamp and ballast assembly which is submerged in the liquid.

Another aspect of the invention provides means for transmission of electrical power and electrical signals, in the form of a laminate which comprises:

a plurality of elongated electrically conducting members, each with a plurality of connectors at spaced apart intervals along the member, said electrically conducting members having an electrically insulating material between the members.

In one embodiment, each electrically conducting member is sandwiched between two electrically insulating strips, and at least one of the strips has notches at spaced apart intervals along the strip, wherein the connectors are housed in the notches.

In another embodiment, the laminate has first and second elongated electrically conducting members, said first electrically conducting member being sandwiched between first and second electrically insulating members and said second electrically conducting member being sandwiched between second and third electrically insulating members.

In a further embodiment, the connectors are spring clip connectors for connecting with electrically conducting pins.

In yet another embodiment, each outer electrically insulating member is clad with a further electrically insulating member.

In another embodiment, the electrically conducting members are metal strips.

DETAILED DESCRIPTION OF PREFERRED EMBODIMENTS

Figure 1:
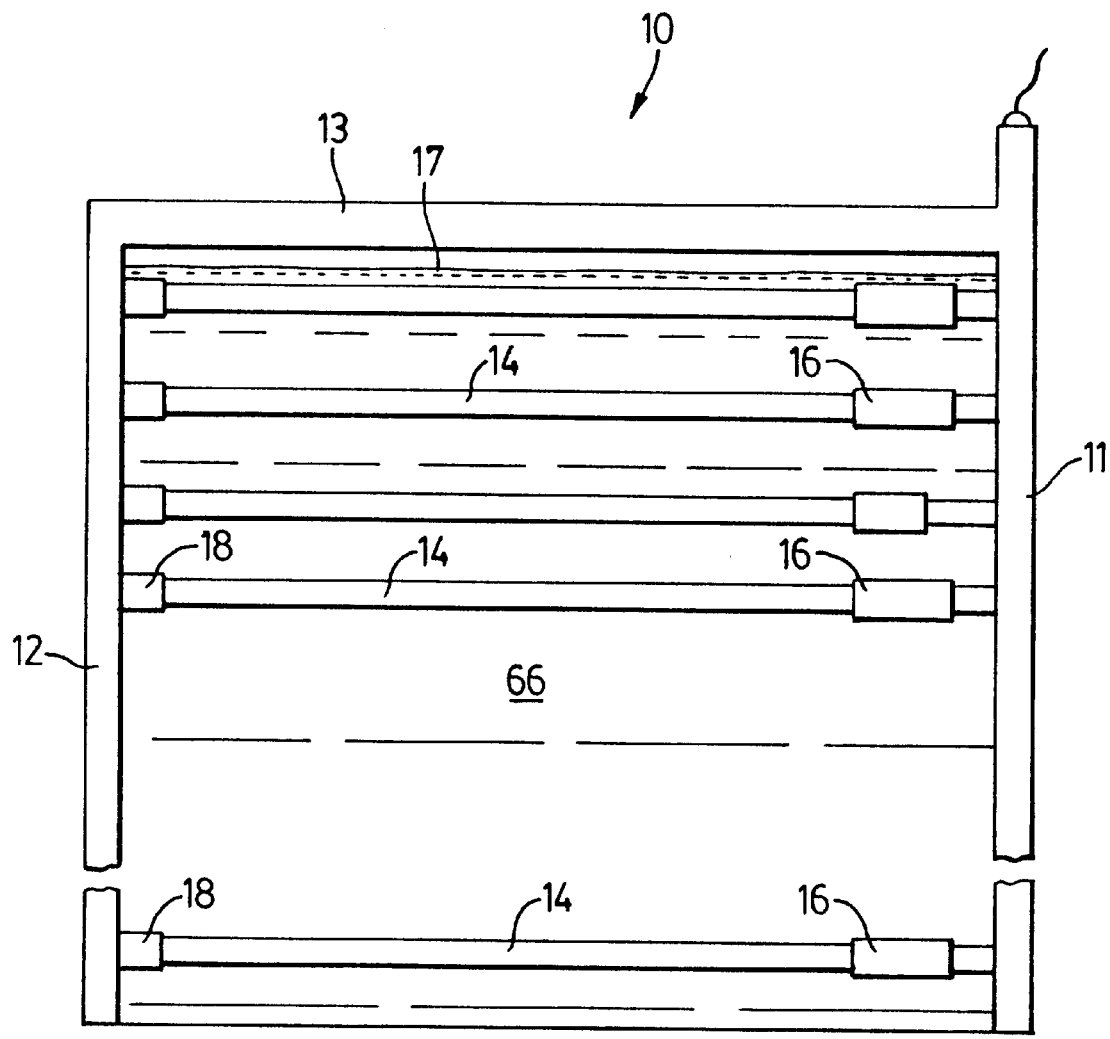
FIG. 1 is a partial side view of a single modular UV lamp rack assembly in accordance with the invention.

Referring to FIG. 1, there is an ultraviolet lamp rack 10 which has a vertical conduit 11, a vertical support member 12 and a bar 13. Located between vertical conduit 11 and vertical member 12 are a plurality of ultraviolet lamps 14 encased in transparent sleeves 15 (partially seen in FIG. 2), with associated ballasts 16 and caps 18. The sleeves 1S are made from a material which permits passage of ultraviolet light. A preferred material is quartz glass. The ultraviolet lamps 14 and ballasts 16 are submerged in liquid 66, e.g waste water. The surface of the liquid is shown at 17 and in FIG. 1 is beneath bar 13.

Figure 2:
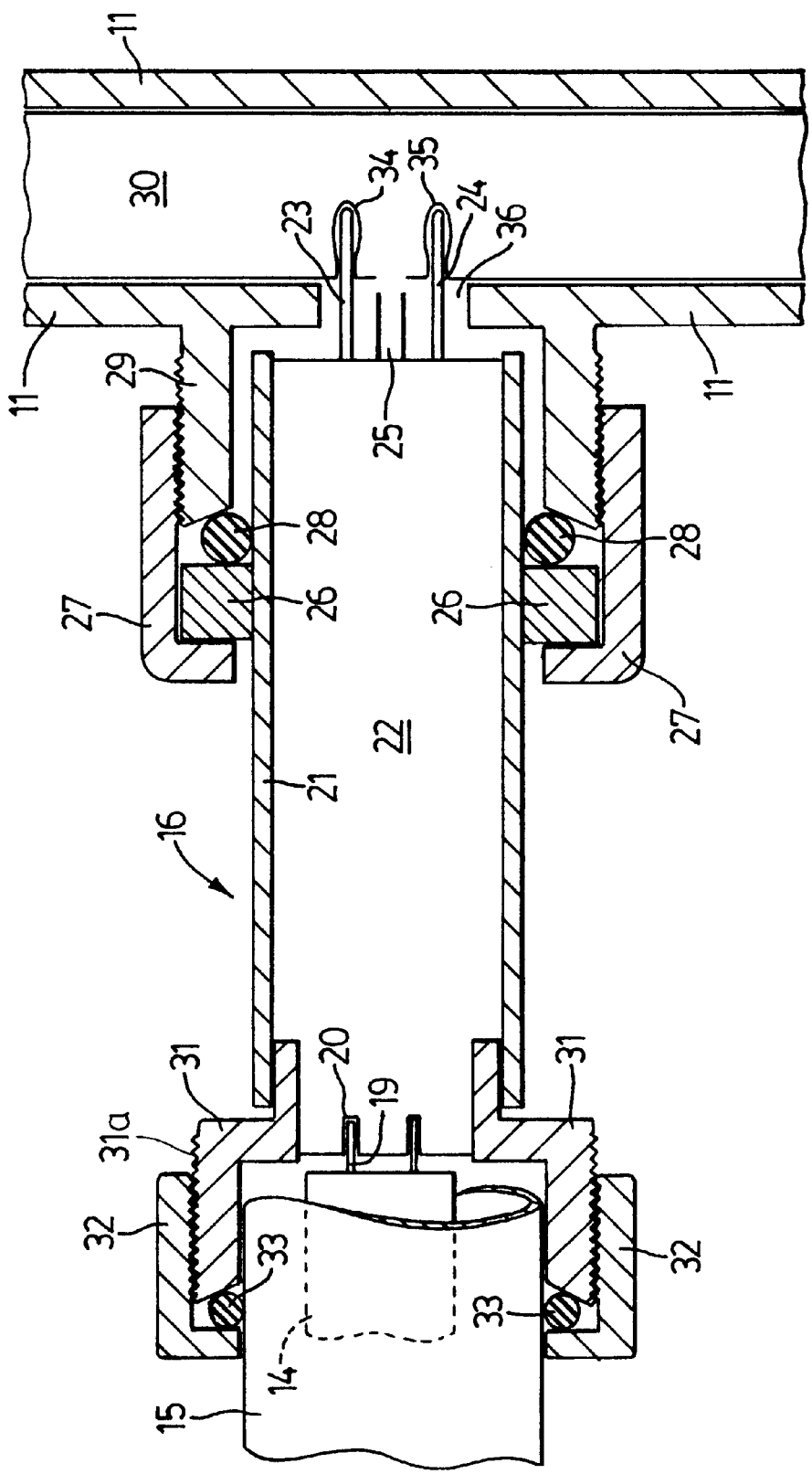
FIG. 2 is a cross-sectional view of a ballast and associated connections in accordance with the invention.

FIG. 2 shows the arrangement of one of the ballasts 16. Ballast 16 has internal components 22 encased in sleeve 21. At one end of ballast 16 there are female electrical connectors 20 for cooperation with electrical pins 19 on ultraviolet lamp 14. At the other end of ballast 16 there is an electrical line pin 23 and an electrical neutral pin 24. Between line pin 23 and neutral pin 24 there is an electrical insulation barrier 25. Attached to sleeve 21 is a retaining ring 26, the purpose of which will be explained hereinafter.

Figure 4:
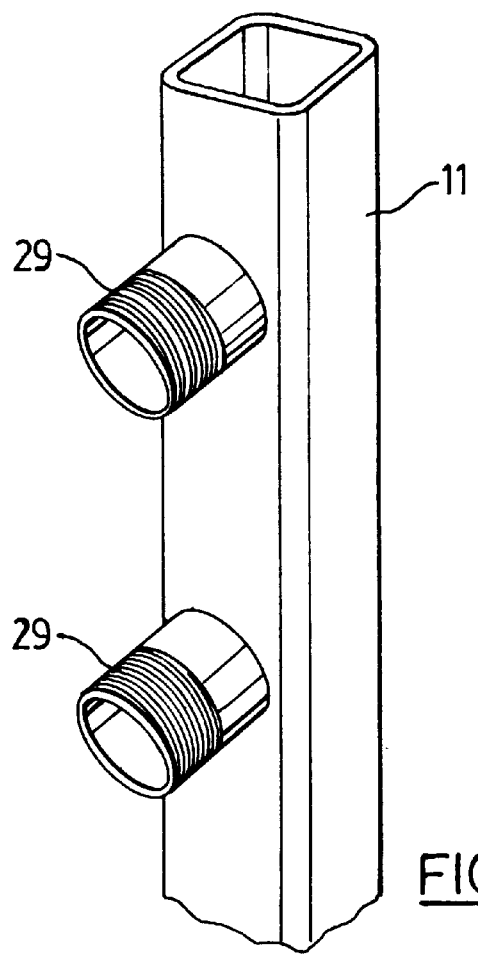
FIG. 4 is a perspective view of a portion of a vertical conduit in a UV lamp rack assembly, useful in the present invention.

FIG. 2 also shows vertical conduit 11 in which there are female electrical connectors 34 and 35, which are electrically connected to electrical conduits, e.g wires, strips. There is an aperture 36 adjacent to connectors 34 and 35, through which pins 23 and 24 may be connected to connectors 34 and 35 respectively. Attached, e.g. welded, to vertical conduit 11 is a tubular stub 29, which has an exterior screw thread, as shown in FIGS. 2 and 4. Ballast 16 is held in place by means of an internally screw threaded coupling 27. The joint between ballast 16 and tubular stub 29 is made watertight by means of an O-ring 28 which is trapped between retaining ring 26 and tubular stub 29.

As indicated above, the ultraviolet light lamp 14 is electrically connected to ballast 16 by means of pins 19 and female connectors 20. At the end of ballast 16 adjacent to the connectors 20, there is a tubular stub 31 which has an external screw thread 31a. Tubular stub 31 is connected to sleeve 21 by a weld or similar. It will be understood that tubular stub 31 may be an integral part of sleeve 21. Quartz sleeve 15 surrounds ultraviolet lamp 14. The connection between the quartz sleeve 15 and tubular stub 31, and thus between ultraviolet lamp 14 and ballast 16, is kept waterproof by means of an O-ring 33 which is trapped between tubular stub 31 and internally threaded retaining nut 32.

It will be understood that other arrangements for securing the ballast and lamps in place are possible without departing from the essence of the invention. For example, sleeve 16 and tubular stub 29 may have the same diameter, and abutting ends may be externally threaded and held together with an internally threaded coupling which screws onto both the sleeve and the stub.

Figure 3:
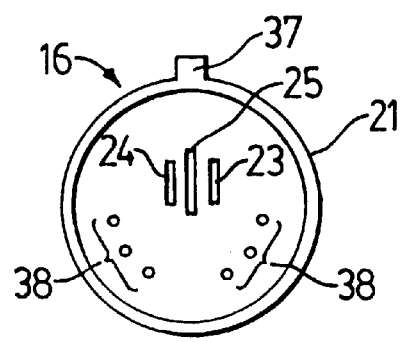
FIG. 3, which is located between FIGS. 1 and 2, is an end view of a ballast used in FIG. 2.

FIG. 3 shows an end of ballast 16, which has line and neutral pins 23 and 24 separated by an electrical insulation barrier 25. The ballast end may have auxiliary pins 38 for alarms and other features.

Figure 5:
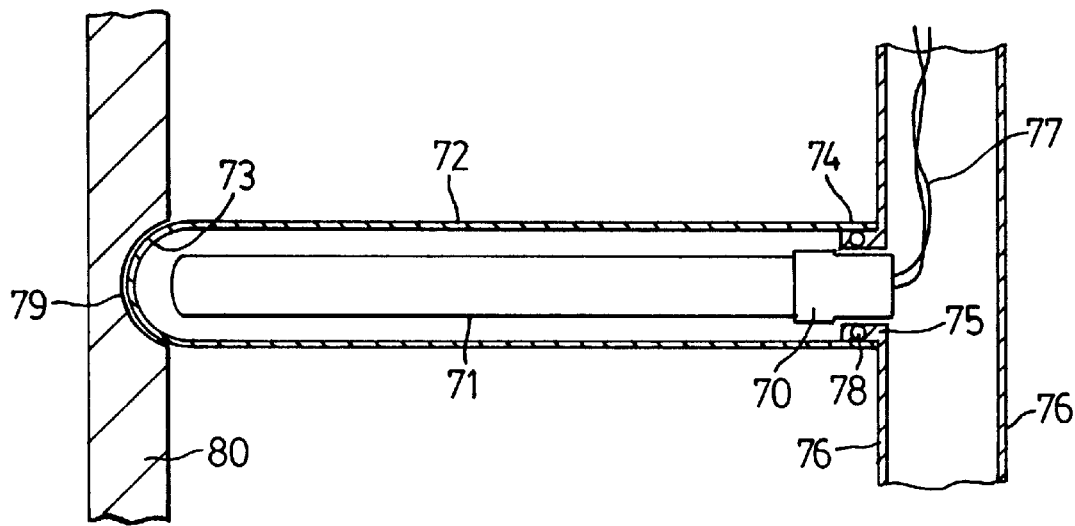
FIG. 5 is a cross sectional view of a ballast and lamp which has an outer sleeve attached to a submersible conduit.
Figure 6:
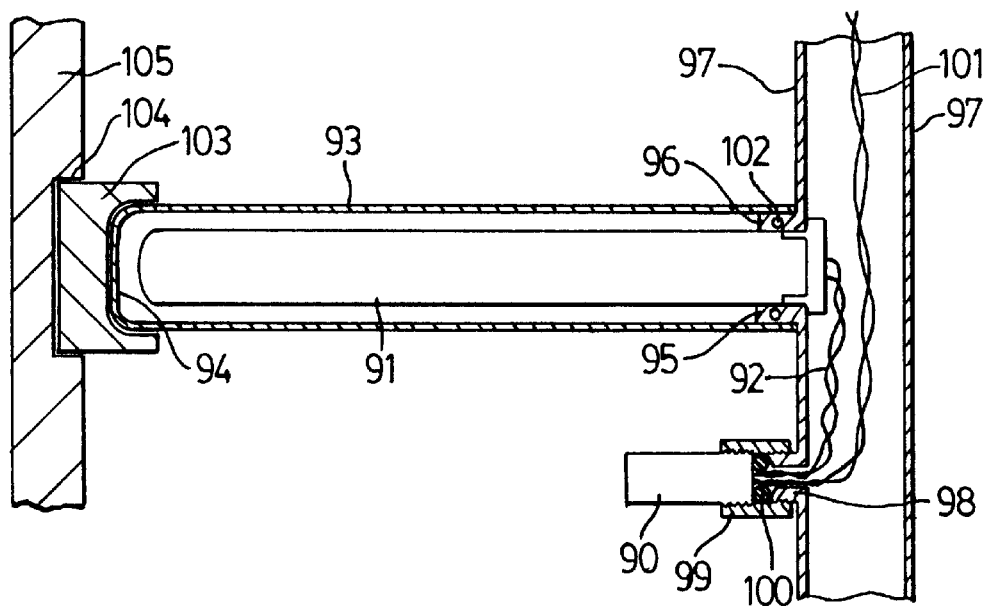
FIG. 6 is a cross-sectional view of a ballast and an associated lamp which are separately attached to a submersible conduit.

FIGS. 5 and 6 illustrate different arrangements of a ballast and an ultraviolet lamp. In FIG. 5, ballast 70 is electrically and mechanically connected to ultraviolet lamp 71. Ballast 70 and lamp 71 are enveloped in sleeve 72. Sleeve 72 has a closed end 73 and an open end 74. open end 74 fits over and is supported by tubular stub 75 which is welded to a vertically arranged tubular conduit 76. There is an aperture in conduit 76 so that there may be electrical communication through conduit 76 to the ballast 70 inside sleeve 72. Electrical communication is accomplished through wires 77 which are appropriately connected to ballast 70. Sleeve 72 is sealed against ingress of fluid, e.g. liquid, outside the sleeve, by means of O-ring 78 or similar. FIG. 5 also shows closed end 73 of sleeve 72 being supported in a cavity 79 in vertically arranged support member 80.

In FIG. 6, ballast 90 is physically separated from ultraviolet lamp 91, although ballast 90 and lamp 91 are electrically connected by wires 92. Lamp 91 is enveloped in sleeve 93. Sleeve 93 has a closed end 94 and an open end 95. Open end 95 fits over and is supported by tubular stub 96 which is welded to vertically arranged tubular conduit 97. There is an aperture in conduit 97 so that there may be electrical communication through conduit 97 to the ballast 90. Ballast 90, which has a threaded end, is mechanically supported by externally threaded stub 98 and internally threaded coupling 99. There is an O-ring 100 trapped between ballast 90 and stub 98 to provided a seal to prevent ingress of fluid into the electrical connections for the ballast and lamp. Ballast 90 has power supply wires 101 connected thereto. Sleeve 93 is sealed against ingress of fluid, e.g. liquid, outside the sleeve, by means of O-ring 102 or similar. Closed end 94 of sleeve 93 has a boot 103 surrounding closed end 94, and boot 103 is supported in a cavity 104 in vertically arranged support member 105.

Figure 7:
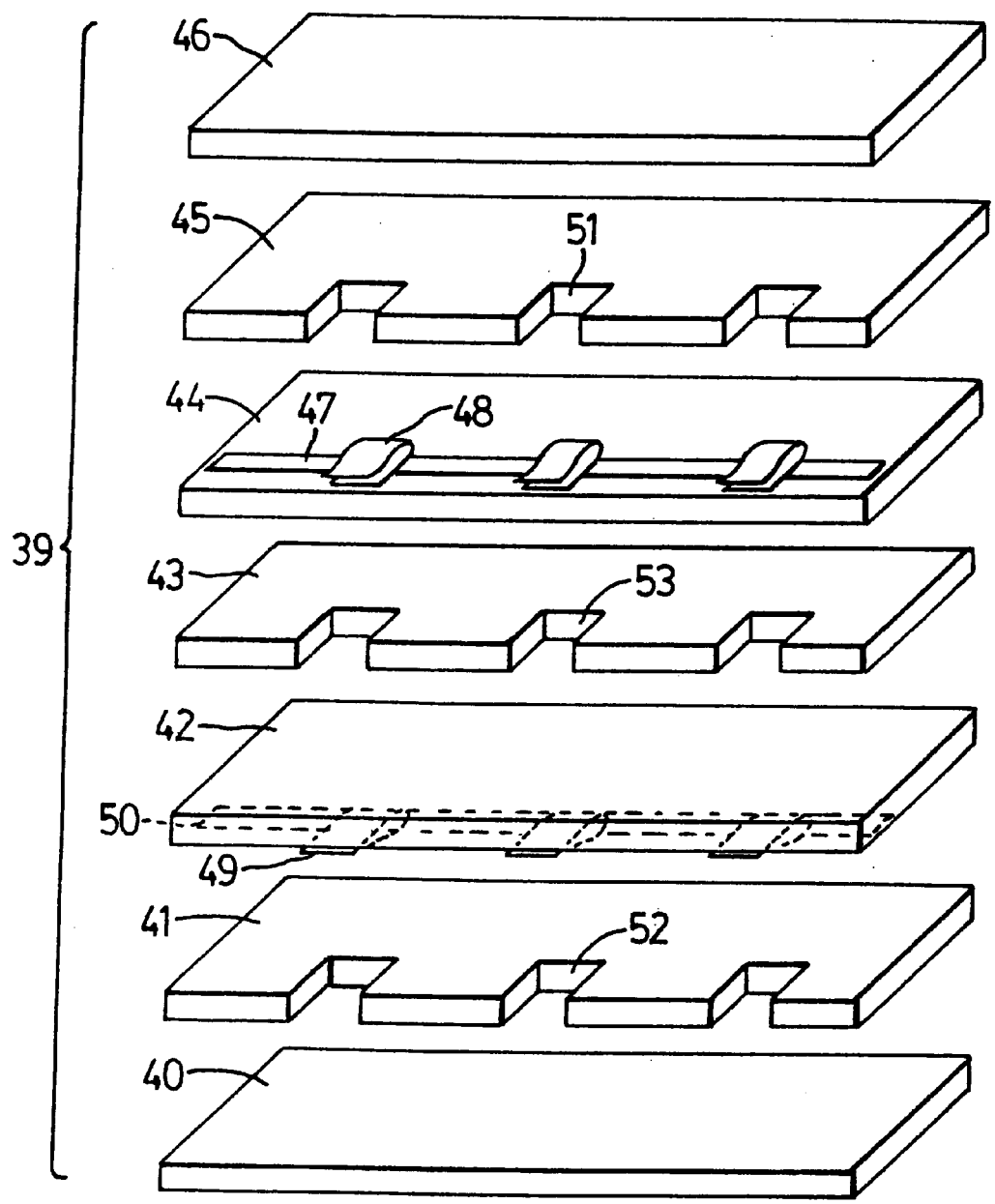
FIG. 7 is an exploded view of a laminate useful as an electrical conduit for use in the present invention.
Figure 8:
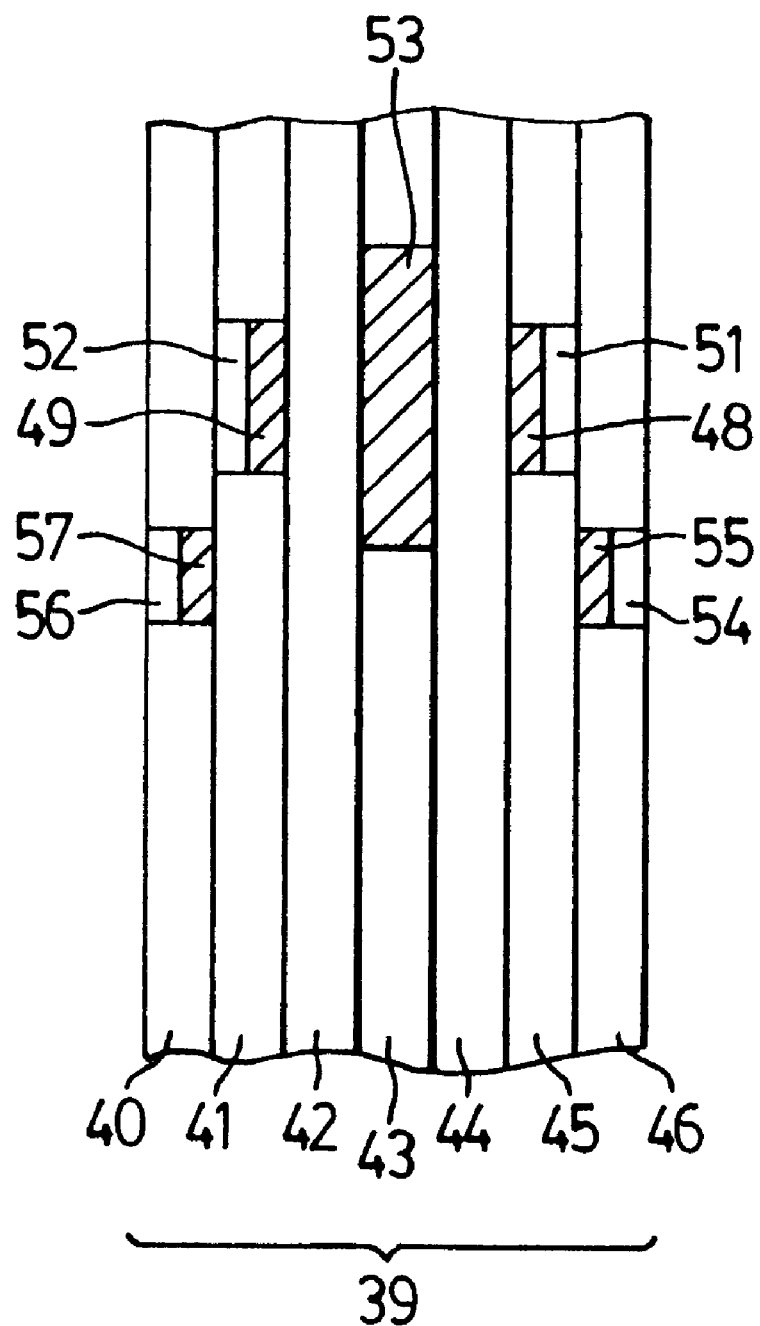
FIG. 8 is a front view of the laminate of FIG. 7, with connecting apertures therein.

FIGS. 7 and 8 illustrate a power and signal laminate 39 which comprises a plurality of strips 40 to 46. The center strip 43 has a notch 53 therein for receiving electrical insulation barrier 25. If there are a plurality of ballasts to be connected to the power and signal laminate, it will be understood that there will be a notch for every ballast. FIG. 7 shows three such notches. Center strip 43 is sandwiched between strips 42 and 44. Strip 42 is sandwiched between strips 43 and 41 and strip 44 is sandwiched between strips 43 and 45. Attached to strip 42, between strips 41 and 42 is an electrically conducting power strip 50 (see FIG. 7) with a plurality of spring clips 49 attached thereto. Attached to strip 44, between strips 44 and 45 is a power strip 47 with a plurality of spring clips 48 attached thereto. Strips 41 and 45 have a plurality of notches 52 and 51 respectively, for reception of electrical pins 23 and 24 respectively. Spring clips 49 nest within notches 52 and spring clips 48 nest within notches 51. Spring clips 48 are for providing secure electrical connection between power strip 47 and electrical pins 24. Spring clips 49 are for providing secure electrical connection between power strip 50 and electrical pins 23. The laminate 39 has outer strips 40 and 46.

The laminate shown in FIG. 8 also has notches 54 and 56 in outer strips 46 and 40 respectively. In notches 54 and 56 there are power strips with spring connectors 55 and 57 respectively therein.

Although not shown, microprocessor chips may be embedded between strips so that the microprocessor chips are protected from the environment, e.g. are protected from water damage. The chips can be used for a variety of purposes, e.g. to monitor the lamps, ballasts, excitation couplers and other electrical or electronic components, and trigger alarms at alarm remote panels.

It will be understood that electrical pins 23 and 24 form an electrical connection with power strips 47 and 50 when pushed into spring clips 48 and 49 respectively. Connectors 55 and 57 are preferably for auxiliary connections, e.g for detection of burnt-out lamps, defective ballasts, leaking joints and the like.

Although the drawings show electrical power being fed to ballasts 16 by means of wires or laminates through conduit 11, electrical power may be fed to ballast 16 through means external to conduit 11. In such an instance, waterproof wires may be used, which enter a waterproof coupling to the ballast. As will be understood, in such an instance, conduit 11 could be replaced by a submersible tube or bar which merely supports ballast 16. Such support may be provided by a flexible or rigid boot attached to the submersible bar. Alternatively, the ballast may be physically separated from the lamp as shown in FIG. 6.

The present invention is useful for the treatment of a wide range of fluids, e.g. gases and liquids. It is preferable that the fluid is flowing around the radiation source and the excitation controlling means. For example, a rack with attached ballasts and ultraviolet lamps is immersed in a flowing gas so that a stream of gas flows over the ultraviolet lamps.

The present invention is particularly useful for the treatment of water, e.g. for waste water disinfection, drinking water disinfection, advanced oxidation treatment and other water treatment processes. The rack with attached ballasts and ultraviolet lamps preferably is immersed in the water so that a stream of water flows over the ultraviolet lamps. Electric power is fed to the lamps via the ballasts, preferably by means of wires or laminates of the present invention through a tubular member of the rack. One of the advantages of this aspect of the present invention is that the water that is being treated can be used to cool the ballasts. This removes the necessity for external forced air cooling or for air conditioning equipment. Furthermore, the ballasts can easily be serviced in situ, removed from service or replaced in the same way that ultraviolet lamps may be serviced or replaced. Any downtime for operation is thus kept to a minimum. In the Ifill et al. apparatus, if a ballast, which is present in vertical conduit 15 becomes defective, all of the ballasts and associated wiring must be removed from the conduit, repaired and then reinserted. The present invention is a great improvement over Ifill's invention and other known systems.

Another advantage of the present invention is that the life of ballasts or excitation couplers should be greater because they are kept cooler.

It will be understood that the present invention is applicable to low pressure standard output lamps, low pressure high output lamps, low pressure triple output (amalgam) lamps, medium pressure lamps, electrodeless lamps and excimer lamps.

Although the drawings have been limited to showing installation of a system with ballasts and ultraviolet lamps, the present invention is equally applicable to other radiation sources and other excitation controlling means. For example, electrodeless ultraviolet lamps or video projection lamps or street lamps may be used with high frequency, e.g. radio frequency, excitation couplers.

While several embodiments of this invention have been illustrated in the accompanying drawings and described hereinabove, it will be evident to those skilled in the art that changes and modifications may be made therein without departing from the essence of this invention, as set forth in the appended claims.

What is claimed is:

1. A radiation source assembly for use in a photochemical treatment of a fluid, comprising:

at least one radiation source adapted to be immersed in said fluid when the assembly is in use, the source producing radiation by excitation of a gas;

an excitation controlling means coupled to each radiation source for controlling excitation of the gas within the radiation source, each excitation controlling means being adapted to be immersed in said fluid to contact said fluid directly so as to be cooled by said fluid when the assembly is in use;

an elongate frame member having a portion adapted to be immersed in the fluid when the assembly is in use, the fame member being connected to at least one of the radiation source and the excitation controlling means; and electrical conducting means coupled to the excitation controlling means for providing electrical energy to the excitation controlling means.

2. A radiation source assembly according to claim 1 wherein the radiation source is an ultraviolet lamp and the excitation controlling means is a ballast electrically connected to the ultraviolet lamp.

3. A radiation source assembly according to claim 2 in which the assembly further comprises an ultraviolet transparent sleeve for each ultraviolet lamp, each ultraviolet lamp being received by a correspond sleeve, said frame member being connected to at least one of a) an ultraviolet lamp, b) an ultraviolet-transparent sleeve; and c) a ballast.

4. A radiation source assembly according to claim 3 wherein the ultraviolet lamp is adjacent to the ballast.

5. A radiation source assembly according to claim 4 wherein the ballast is supported by said elongate frame member.

6. A radiation source assembly according to claim 5 for use in treating a liquid, wherein each ballast is elongate and has first and second opposed ends, the first end being mounted on said portion of the elongate frame member adapted to be immersed in the liquid, and wherein each lamp is elongate and has first and second opposed ends, the first end of each lamp being connected to the second end of a corresponding ballast.

7. A radiation source assembly according to claim 6 wherein the assembly comprises a second elongate frame member for supporting the second end of each lamp.

8. A radiation source assembly according to claim 6 wherein said elongate frame member is tubular with an outer wall and wherein there is, for each ballast, a support with an externally threaded tubular stub surrounding an access aperture through the outer wall, the ballast having an external retaining ring fixed adjacent the first end thereof, the assembly further comprising an internally threaded coupling for engaging the stub and the retaining ring, so as to move the stub and the ring toward each other, and a resilient sealing member between the stub and the coupling such that the retaining ring is pressed against the exterior of the excitation controlling means when the coupling is tightened.

9. A radiation source assembly according to claim 6 wherein each sleeve has one open end and one closed end, said radiation source assembly further comprising a coupling which sealingly supports the open end of each sleeve from the second end of the ballast.

10. A process for treating liquids with ultraviolet light comprising passing the liquid over a radiation source assembly according to claim 1 which is at least partially immersed in the liquid.

11. A radiation source assembly according to claim 1 wherein said electrical conducting means comprises a laminate having a plurality of elongated electrically conducting members, each member having a plurality of electrical connectors at spaced apart intervals along the member, said laminate having electrically insulating material between the members.

12. A radiation source assembly according to claim 11 wherein each electrically conducting member is sandwiched between two electrically insulating strips, at least one of the strips having notches at spaced apart intervals along the strip for receiving said connectors therein.

13. A radiation source assembly according to claim 11 wherein said connectors are spring clip connectors for connecting with electrically conducting pins.

14. A radiation source assembly according to claim 2 wherein the electrical conducting means includes, for each excitation controlling means, an electrical wire which extends from the excitation controlling means to a location which is not immersed in the fluid.

15. A radiation source assembly for use in a photochemical treatment of a fluid comprising:

at least one ultraviolet lamp for producing radiation by excitation of a gas;

a ballast coupled to each lamp and adapted to be immersed in said fluid to contact said fluid directly so as to be cooled by said fluid when the assembly is in use, each blast functioning to control the excitation of the gas within the corresponding lamp;

an ultraviolet transparent sleeve for each lamp, each sleeve receiving a respective lamp therein;

a submersible frame member having a portion adapted to be immersed in the fluid when the assembly is in use and having a plurality of supports, each support providing support for at least one of a) an ultraviolet lamp, b) an ultraviolet-transparent sleeve and c) a ballast; and electrical conducting means coupled to the ballast for providing electrical energy to the ballast.

16. A radiation source assembly according to claim 15 further comprising a screw coupling for sealingly connecting each sleeve to a corresponding ballast.

17. A radiation source assembly according to claim 15 wherein the frame member contains said electrical conducting means and the ballast is removably coupled, electrically, to said electrical conducting means.

\* \* \* \* \*